US00PP34650P2

(12) United States Plant Patent
Elsworth

(10) Patent No.: US PP34,650 P2
(45) Date of Patent: Oct. 11, 2022

(54) ***AJUGA* PLANT NAMED 'FANFIN'**

(50) Latin Name: ***Ajuga reptans* x *Ajuga tenorii***
Varietal Denomination: Fanfin

(71) Applicant: Kelly Elsworth, Portage, MI (US)

(72) Inventor: Kelly Elsworth, Portage, MI (US)

(73) Assignee: Christopher M. Hansen, Zeeland, MI (US)

( * ) Notice: Subject to any disclaimer, the term of this patent is extended or adjusted under 35 U.S.C. 154(b) by 0 days.

(21) Appl. No.: 17/687,273

(22) Filed: Mar. 4, 2022

(30) Foreign Application Priority Data

Dec. 22, 2021 (QZ) ..... PBR 20213429

(51) Int. Cl.
*A01H 5/02* (2018.01)
*A01H 6/50* (2018.01)

(52) U.S. Cl.
USPC ..... Plt./401

(58) Field of Classification Search
USPC ..... Plt./401
See application file for complete search history.

(56) References Cited

PUBLICATIONS https://online.plantvarieties.eu/publicSearch—CPVO Register—CPVO Application Consultation—Citation for 'Finfan' Retrieved from the Internet Apr. 22, 2022 (version 4.1.49) (3 pages ).*

* cited by examiner

*Primary Examiner* — Susan McCormick Ewoldt
(74) *Attorney, Agent, or Firm* — Penny J. Aguirre

(57) ABSTRACT

A new cultivar of *Ajuga* plant named 'Fanfin' that is characterized by its foliage that emerge apricot-bronze in color, change to lime-yellow-green in color and finally mature to lime green in color with the foliage colors presented on a plant at the same time for a tri-colored effect, its winter foliage that is coppery bronze in color, its vigorous growth habit, its cobalt blue flowers that bloom in late spring, and its high resistance to sun scorch and thrives in full sun in the summer.

2 Drawing Sheets

Botanical classification: *Ajuga reptans* x *Ajuga tenorii*.
Variety denomination: 'Fanfin'.

CROSS-REFERENCE TO RELATED APPLICATIONS

This application claims priority to European Community Plant Variety Office (CPVO) Plant Breeder's Rights Application No. 2021/3429 filed on Dec. 22, 2021, under 35 U.S.C. 119(f), the entire contents of which is incorporated by reference herein. This application is co-pending with a U.S. Plant Patent Application filed for plants derived from the same breeding program that is entitled *Ajuga* Plant Named 'Corcan' (U.S. Plant patent application Ser. No. 17/687,232).

BACKGROUND OF THE INVENTION

The present invention relates to a new and distinct cultivar of *Ajuga* of hybrid origin and will be referred to hereafter by its cultivar name, 'Fanfin'. 'Fanfin' represents a new cultivar of *Ajuga*, an herbaceous perennial grown for landscape use.

The new Invention arose from an ongoing controlled breeding program in Hudsonville, Mich. The objective of the breeding program is to develop new cultivars of *Ajugas* with unique foliage coloration, different leaf sizes and strong clump forming growth habits. The new cultivar arose from a controlled cross made between an unnamed and unpatented plant of *Ajuga reptans* with gold foliage as the female parent and *Ajuga tenorii* 'Chocolate Chip' (not patented) as the male parent. The Inventor selected 'Fanfin' as a single unique plant from amongst the seedlings of the above cross in May of 2020.

Asexual propagation of the new cultivar was first accomplished by stem tip cuttings in June of 2020 in Hudsonville, Mich. Propagation by stem tip cuttings and division has determined the characteristics to be stable and reproduced true to type in successive generations.

SUMMARY OF THE INVENTION

The following traits have been repeatedly observed and are determined to be the characteristics of the new cultivar. These attributes in combination distinguish 'Fanfin' as a unique cultivar of *Ajuga*.

1. 'Fanfin' exhibits foliage that emerge apricot-bronze in color, change to lime-yellow-green in color and finally mature to lime green in color with the foliage colors presented on a plant at the same time for a tri-colored effect.
2. 'Fanfin' exhibits winter foliage that is coppery bronze in color.
3. 'Fanfin' exhibits a vigorous growth habit.
4. 'Fanfin' exhibits cobalt blue flowers that bloom in late spring.
5. 'Fanfin' exhibits a high resistance to sun scorch and thrives in full sun in the summer.

The female parent plant of 'Fanfin' differs from 'Fanfin' in having leaves that are much larger in size and yellow in color, flowers that are pink in color, and a larger plant size.

The male parent plant of 'Fanfin' differs from 'Fanfin' in having foliage that is purple in color. 'Fanfin' can be most closely compared to *Ajuga tenorii* cultivar 'Mint Chip' (U.S. Plant Pat. No. 20,734) and *Ajuga* 'Corcan'. 'Mint Chip' is similar to 'Fanfin' in having flowers that are blue in color and a similar leaf shape and size. 'Mint Chip' differs from 'Fanfin' in having foliage that is green in color. 'Corcan' is similar to 'Fanfin' in having flowers that are blue in color and in being a hardy groundcover. 'Corcan' differs from 'Fanfin' in having foliage that is yellow in color and in producing many less flowers per plant.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but are not limited to website publications by Spring Hill Nursery, Romence Gardens, Bloomin Designs, Michigan Bulb, Winter Green House, Great Garden Plants, Wilson Bros Gardens, Mountain Crest Gardens, In the Country Garden and Gifts, WalMart, Garden Crossings, Garden Solutions Plants, Plant Central, Peace Tree Farm, Quality Cuttings, White House Plants, Millette Photo Media, Garden Center Ohio, Amazon, Evergreen Nursery Inc, Pinterest, Chicago Botanic, Emerisa, Creekside Gardens Inc, Phoenix Perennials, Earth, Baker Sacres Greenhouse, 2 Bing, You Tube, Houzz, George Weigel, Milled, Rideau Woodland Ramble, Gateway Gardens, Fermebedardblouin, Get Blooming, Green Profit, Express Seed, bhg, thursd, Preen, O Canada, Greenland Garden, Peconicrive Herb Farm, Barsons, svgplants, The Observer, Germania Seed, Windor Star, ehrnet, Multi Screen Site, degroots, Sherwoods Forests, Garden Works, Zyromski, and rslandscape design.

BRIEF DESCRIPTION OF THE DRAWINGS

The accompanying color photographs illustrate the overall appearance and distinct characteristics of the new *Ajuga* as grown in a greenhouse in Hudsonville, Mich. The photographs in FIG. 1 and FIG. 2 were taken of a 2-year-old plant of 'Fanfin' as grown in a 1-gallon container and the photograph in FIG. 3 was taken of a 1-year-old plant of 'Fanfin' as grown in a 1-quart container.

The photograph in FIG. 1 provides a side view of a plant 'Fanfin' in bloom.

Figure 1:
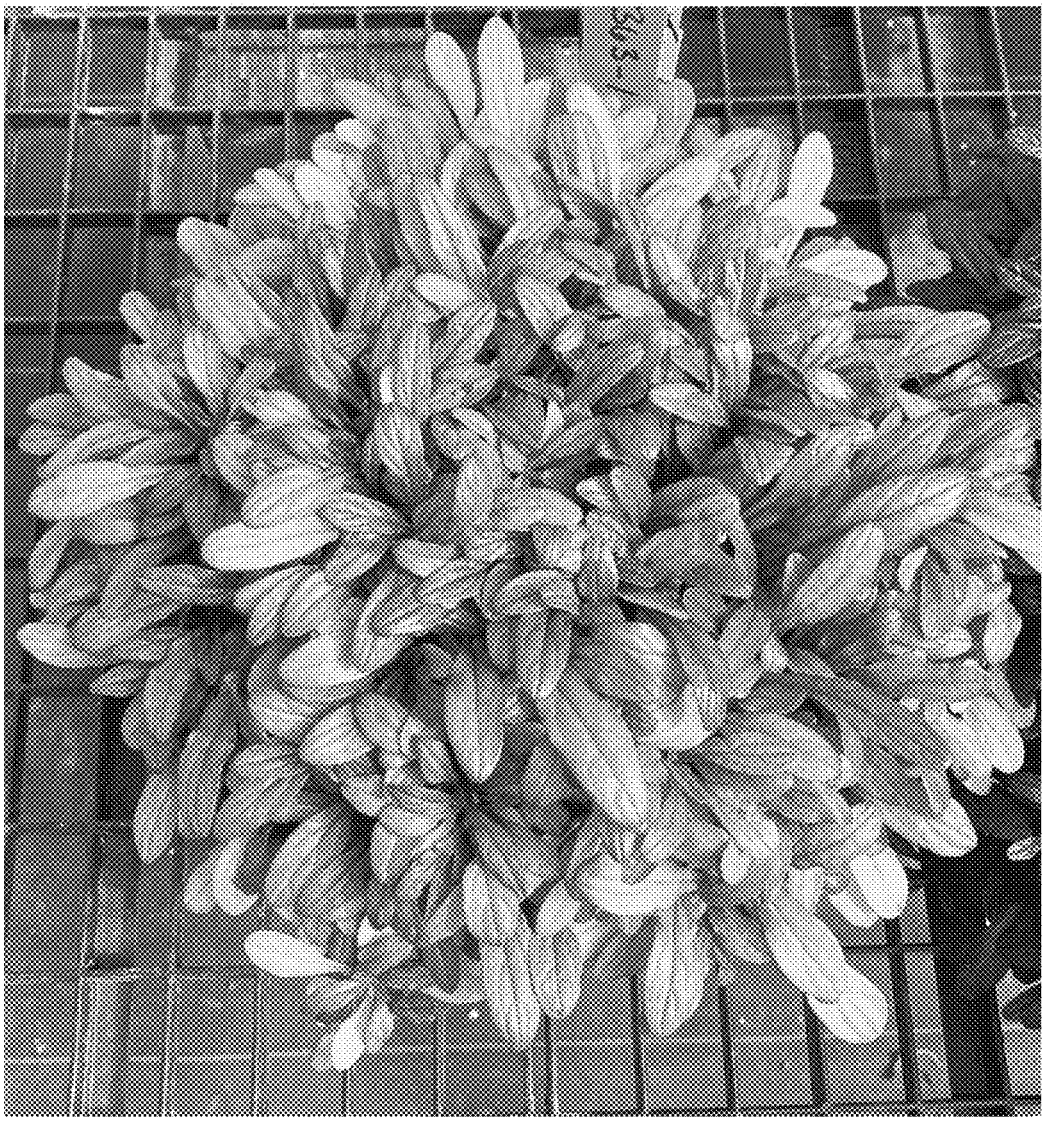
Figure 2:
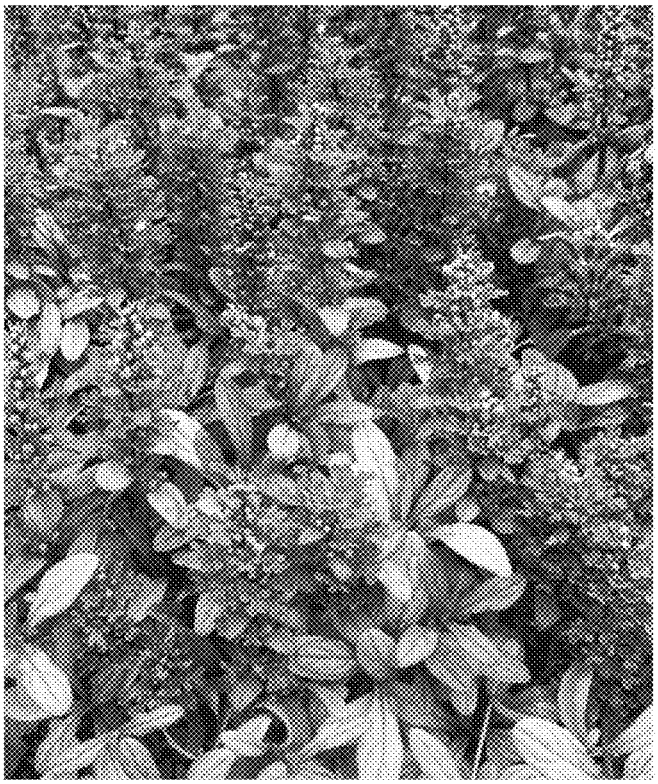

The photograph in FIG. 2 provides a close-up view of the foliage of 'Fanfin'.

Figure 3:
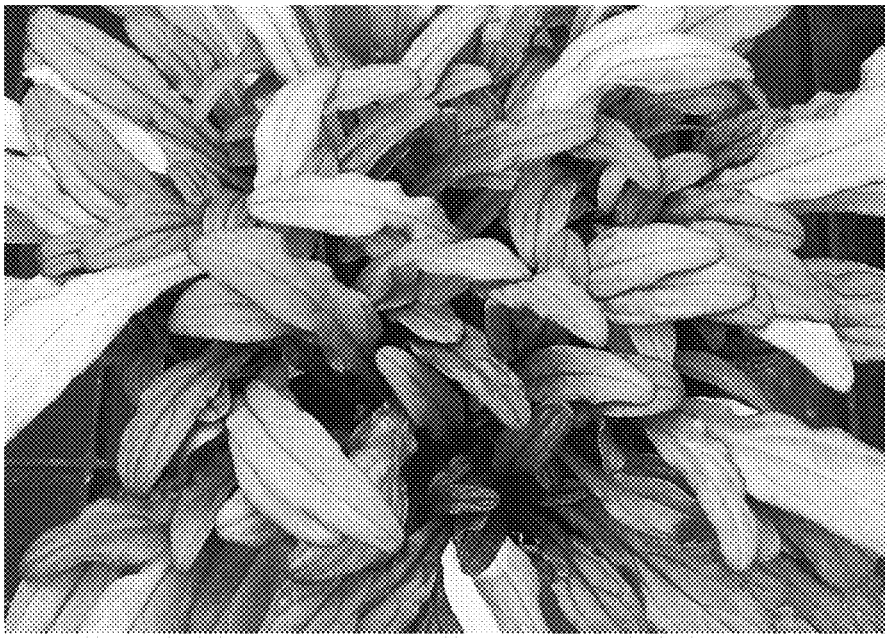

The photograph in FIG. 3 provides a close-up view of the winter foliage of 'Fanfin'.

The colors in the photograph may differ slightly from the color values cited in the detailed botanical description, which accurately describe the colors of the new *Ajuga*.

DETAILED BOTANICAL DESCRIPTION

The following is a detailed description of the new cultivar as observed on 6-month-old plants of the new *Ajuga* as grown in 4-inch containers in a greenhouse in Hudsonville, Mich. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—4 to 6 weeks in late spring into summer in Michigan.

*Plant type.*—Herbaceous perennial.

*Plant habit.*—Dense and rounded, compact upright inflorescences.

*Height and spread.*—13 cm in height (soil level to top of floral plane), an average of 9 cm in height (soil level to top of foliar plane) and 13 cm in width, a mature plant in the landscape reaches an average of 10 cm in height and 46 cm in spread.

*Cold hardiness.*—At least in U.S.D.A. Zones 4 to 8.

*Diseases and pests.*—Plants have been observed to be disease free, however no resistance to any specific diseases is known, no resistance or susceptibility to pests has been observed.

*Root description.*—Fine and fibrous, a blend of 158A and NN155A in color.

*Propagation type.*—Tip stem cuttings and division.

*Root development.*—An unrooted stem cutting will fully root in a 50-cell plug in 8 weeks and a 50-cell plug will fully root in a 1-gallon container in 10 weeks.

*Growth rate.*—Vigorous.

*Branching habit.*—Basal rosettes of leaves from rhizomes.

Foliage description:

*Leaf shape.*—Spatulate.

*Leaf division.*—Simple.

*Leaf base.*—Truncate to base of rhizome.

*Leaf apex.*—Broadly acute to rounded.

*Leaf venation.*—Pinnate, matches surface colors.

*Leaf margins.*—Entire to slightly undulate.

*Leaf attachment and arrangement.*—Whorled, held in in clumps.

*Leaf orientation.*—Emerge upright and then slightly outward.

*Leaf surface.*—Very finely puberulent and slightly rough to the touch on upper and lower surface.

*Leaf color.*—Young upper surface; 137A, base N144A, young lower surface; 144A, mature upper surface; 144A, becoming flushed with 183A and then fully changing to 187A as the leaf ages, mature lower surface; 138B, becoming flushed with a blend of 185A and 186A as the leaf ages, winter foliage; blend of 187C, N144A, and 166C (effectively appearing bronze).

*Leaf size.*—Average of 7 cm in length, 7 mm in width.

*Leaf quantity.*—Average of 30 in a clump 1.5 cm in diameter.

*Leaf attachment.*—Sessile.

Flower description:

*Inflorescence type.*—Verticillaster, terminal spike, individual flowers in clusters held in leaf-axils.

*Inflorescence size.*—An average of 7 cm in height and 2.5 cm in width.

*Inflorescence number.*—70 to 90 as a fully mature plant grown in a 1-gallon container.

*Lastingness of inflorescence.*—10 to 14 days, self-cleaning.

*Flower type*.—Labiate.

*Flower number*.—Average of 30 per inflorescence.

*Flower fragrance*.—None.

*Flower buds*.—Oblanceolate in shape, average of 5 mm in length and 2 mm in diameter, color; 145C, at bud burst 91C, immature calyx 145C, surface matte and densely covered with soft woolly pubescence.

*Flower size*.—Average of 1 cm in depth, 5 mm in diameter, throat diameter 2 mm, tube 4 mm in length and 1.5 mm in diameter.

*Peduncles*.—An average of 5 cm in length, 2 mm in diameter, vertical angle, moderately strong, color; a blend of 145A, 186A and 185A, surface is glossy and sparsely covered with very short hairs that match surface color.

*Calyx*.—Rotate and tubular in shape, 2 mm in length and diameter.

*Sepals*.—5, 50% fused at base, average of 1.5 mm in length, 1 mm in width, ovate in shape, apex acute, entire margins, surface is covered with long woolly hairs matching surface color, color inner and outer surface 145A.

*Petals*.—50% of petals fused into tube, upper central lobe; notched, average of 5 mm in length, 2 mm in width, blunt and rounded in shape, obtuse apex, entire margins, no undulation, upper and lower surface glabrous, slightly glossy, color; upper surface when opening and fully open 91B, flushed with 91A, veins 90A, lower surface when opening and fully open 91A, outer lobes; 2, average of 4 mm in length, 2 mm in width, oblanceolate in shape, apex is obtuse, entire margins, no undulation, upper and lower surface glabrous and slightly glossy, color; upper surface when opening and fully open 91B, flushed with 91A, veins 90A, flower throat; outer surface covered with woolly soft pubescence, inner surface is smooth and glabrous, color; inner and outer surface when opening and fully open 92B, flower tube; inner and outer surface glabrous, color inner and outer surface when opening and fully open 92D.

Reproductive organs:

*Pistils*.—1, style; 6 mm in length, 92D in color, base NN155D in color, stigma; non-distinguishable, ovary; oblong, 2 mm in length, 1 mm in width, NN155D in color.

*Stamens*.—5, filament; implanted into flower tube, average of 5 mm in length, NN155D in color, anthers; club-shaped, 0.5 mm in diameter, 203A in color, pollen; none observed.

*Fruit*.—Fruit and seed production has not been observed to date.

It is claimed:

1. A new and distinct variety of *Ajuga* plant named 'Fanfin' as described and illustrated herein.

* * * * *